(12) United States Patent
Kalkhoran

(10) Patent No.: US 10,292,790 B2
(45) Date of Patent: May 21, 2019

(54) ION IMPLANTATION MODIFICATION OF ARCHWIRES

(71) Applicant: N2 Biomedical LLC, Bedford, MA (US)

(72) Inventor: Nader M. Kalkhoran, Tewksbury, MA (US)

(73) Assignee: N2 Biomedical LLC, Bedford, MA (US)

( * ) Notice: Subject to any disclaimer, the term of this patent is extended or adjusted under 35 U.S.C. 154(b) by 5 days.

(21) Appl. No.: 15/391,060

(22) Filed: Dec. 27, 2016

(65) Prior Publication Data

US 2017/0181813 A1    Jun. 29, 2017

Related U.S. Application Data

(60) Provisional application No. 62/271,377, filed on Dec. 28, 2015.

(51) Int. Cl.
| | |
|---|---|
| *A61C 7/00* | (2006.01) |
| *A61C 7/20* | (2006.01) |
| *C23C 14/48* | (2006.01) |
| *C23C 14/06* | (2006.01) |

(52) U.S. Cl.
CPC ............ *A61C 7/20* (2013.01); *C23C 14/0605* (2013.01); *C23C 14/48* (2013.01)

(58) Field of Classification Search
CPC ........ A61C 7/20; C23C 14/0605; C23C 14/48
See application file for complete search history.

(56) References Cited

U.S. PATENT DOCUMENTS

| 5,091,655 A | * | 2/1992 | Dykstra | H01J 37/12 250/398 |
| 5,288,230 A | * | 2/1994 | Nikutowski | A61C 7/12 433/20 |
| 8,673,753 B1 | * | 3/2014 | Wan | H01J 37/3171 438/514 |
| 9,741,894 B2 | * | 8/2017 | Adibi | C23C 14/042 |
| 2003/0200930 A1 | * | 10/2003 | Chen | H01J 37/3171 118/723 FI |
| 2005/0087516 A1 | * | 4/2005 | Duerksen | H01L 21/26586 216/62 |
| 2007/0142498 A1 | * | 6/2007 | Brennan | A61K 6/0023 523/118 |
| 2008/0074643 A1 | * | 3/2008 | Chen | A61C 7/00 356/32 |
| 2009/0032499 A1 | * | 2/2009 | Tenne | A61C 7/14 216/109 |

(Continued)

*Primary Examiner* — Nicholas D Lucchesi
(74) *Attorney, Agent, or Firm* — Hunter Clark PLLC

(57) ABSTRACT

Techniques and methods for utilizing ion implantation to modify dental archwires are provided. An example of a method of ion implanting a wire target includes providing the wire target in an ion implant system, implanting ions into the wire target such that a color of the wire target material after the implanting exhibits a changed appearance from the color of the wire target material before the implanting, and removing the wire target from the ion implant system. An example of a copper-aluminum-nickel (CuAlNi) wire includes an ion implanted atomic species wherein a color of an implanted CuAlNi wire is white, off-white and/or silver and further wherein the implanted CuAlNi wire exhibits mechanical properties of an unimplanted CuAlNi wire.

8 Claims, 8 Drawing Sheets

(56) References Cited

U.S. PATENT DOCUMENTS

| | | | |
|---|---|---|---|
| 2010/0028823 A1* | 2/2010 | Reid | A01N 55/00 |
| | | | 433/6 |
| 2010/0173256 A1* | 7/2010 | Rodriguez | A61C 7/141 |
| | | | 433/10 |
| 2010/0330522 A1* | 12/2010 | Hirsch | A61C 7/00 |
| | | | 433/8 |
| 2013/0280669 A1* | 10/2013 | Cinader | A61C 7/14 |
| | | | 433/9 |
| 2014/0227653 A1* | 8/2014 | Kalkhoran | A61C 7/20 |
| | | | 433/8 |
| 2014/0272754 A1* | 9/2014 | Curley | A61C 7/20 |
| | | | 433/11 |

* cited by examiner

| Ion Beam Dose | Ion Beam Dose Rate | Ion Implant Duration | Ion Beam Energy |
|---|---|---|---|
| 12D | R | 12T | E |
| 4D | R | 4T | E |
| D | R | T | E |
| D | 0.5R | 2T | E |
| D | 0.25R | 4T | E |
| D | 0.5R | 2T | 0.5E |
| 0.5D | 0.5R | T | 0.5E |
| D | 0.25R | 4T | 0.5E |
| 0.5D | 0.25R | 2T | 0.5E |
| 0.1D | 0.25R | 0.4T | 0.5E |

D= 5E16 ions/cm$^2$

R=0.1 µA/cm$^2$/sec

E=80keV

T=1 hour

*FIG. 6*

ION IMPLANTATION MODIFICATION OF ARCHWIRES

CROSS-REFERENCE TO RELATED APPLICATIONS

This application claims the benefit of U.S. Provisional Application No. 62/271,377 filed Dec. 28, 2015, entitled "ION IMPLANTATION MODIFICATION OF ARCHWIRES," the entire contents of which is hereby incorporated herein by reference.

BACKGROUND

As a component of orthodontic treatment, archwires provide the forces that correct irregularities in tooth positioning. However, the archwire materials that provide the desired mechanical forces may not be aesthetically pleasing to patients with regard to color. There is a market demand for aesthetically pleasing archwires with regard to wire color. Coated archwires may be used to satisfy this demand. However, despite their favorable appearance, coated archwires may have a number of drawbacks. For instance, coated archwires may not provide desired force characteristics and/or may be prone to breakage and/or the coating may wear away or delaminate before the wire has reached its functional lifetime.

SUMMARY

The following summarizes some aspects of the present disclosure to provide a basic understanding of the discussed technology. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in summary form as a prelude to the more detailed description that is presented later.

An example of a method of ion implanting a wire target according to the disclosure includes providing the wire target in an ion implant system, implanting ions into the wire target such that a color of the wire target material after the implanting exhibits a changed appearance from the color of the wire target material before the implanting, and removing the wire target from the ion implant system.

Implementations of the method may include one or more of the following features. The wire target may be a copper-aluminum-nickel (CuAlNi) alloy. The implanting ions may include implanting ions at an ion beam dose of 1E15-1E18 ions/$cm^2$, an ion beam dose rate of 0.025-10 $\mu A/cm^2$/sec, an ion implant duration of 0.4-12 hours, and an ion beam energy of 10-200 keV. The implanting ions may include implanting one or more of C, CO, Si, O, F, N, B, H or combinations thereof.

The method may include implanting carbon ions at an ion beam dose of approximately 5E16 ions/$cm^2$, an ion beam dose rate of approximately 0.1 $\mu A/cm^2$/sec, an ion implant duration of approximately one hour, and an ion beam energy of approximately 80 keV. The method may include maintaining a temperature of the wire target at or below a particular temperature. The wire target may be a shape memory alloy and the particular temperature may correspond to at least one of a transformation temperature of the wire target or a temperature below 300 degrees Celsius. The mechanical properties of the wire target may be substantially unchanged by the implanting ions into the wire target.

An example of a copper-aluminum-nickel (CuAlNi) wire according to the disclosure includes an ion implanted atomic species wherein a color of an implanted CuAlNi wire is white, off-white and/or silver and further wherein the implanted CuAlNi wire exhibits mechanical properties of an unimplanted CuAlNi wire.

Implementations of the CuAlNi wire may include one or more of the following features. The ion implanted atomic species may be carbon. A penetration depth of an ion implanted region is less than or equal to approximately one micrometer. The CuAlNi wire may be an orthodontic archwire. The CuAlNi wire may exhibit properties of the unimplanted shape memory alloy that are suitable for orthodontic applications.

An example of a method of using an ion implanted archwire according to the disclosure includes installing the ion implanted archwire into orthodontic brackets. The method may include one or more of the following features. The method may include attaching the orthodontic brackets to teeth. The ion implanted archwire may be a C ion implanted CuAlNi archwire. The ion implanted archwire may be a CuAlNi archwire that exhibits at least one of a white, an off-white, or a silver color.

Items and/or techniques described herein may provide one or more of the following capabilities, as well as other capabilities not mentioned. A color appearance of a wire target is modified using an ion implant process. The wire target may be a copper-aluminum-nickel (CuAlNi) alloy wire and the ion implanted atomic species may be carbon (C). The ion implant process may provide the capability of modifying the color of the wire target. The modified color of the ion implanted CuAlNi wire may be different than a copper color generally associated with the CuAlNi alloy. The modified color of the CuAlNi wire may be a white, off-white, and/or silver color. The modified color appearance may provide the advantage of the archwire color being similar to the color of an orthodontic bracket and/or to a natural color of teeth. As a result, the ion implanted CuAlNi wire may be more desirable and marketable to orthodontists and patients than the unimplanted wire. Further, the ion implant may change the color without substantial changes to the mechanical and/or physical properties of the wire. In particular, the shape memory characteristics and other mechanical characteristics with regard to orthodontic applications may be substantially unchanged. Further, in contrast to a coated wire, the color change produced by the ion implant is an intrinsic property of the implanted wire. This may provide advantages of improved durability and longevity of the implanted wire as compared to the coated wire. Other capabilities may be provided and not every implementation according to the disclosure must provide any, let alone all, of the capabilities discussed. Further, it may be possible for an effect noted above to be achieved by means other than that noted and a noted item/technique may not necessarily yield the noted effect.

Other aspects, features, and embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as device, system, or method embodiments it should be understood that such exemplary embodiments can be implemented in various devices, systems, and methods.

BRIEF DESCRIPTIONS OF THE DRAWINGS

Figure 3A:
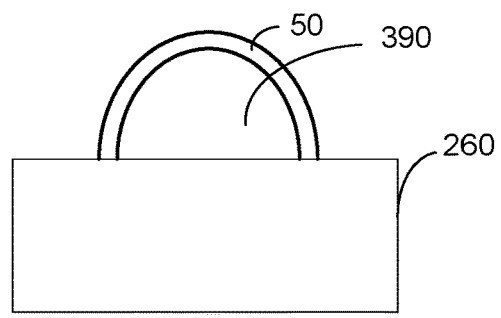
Figure 3B:
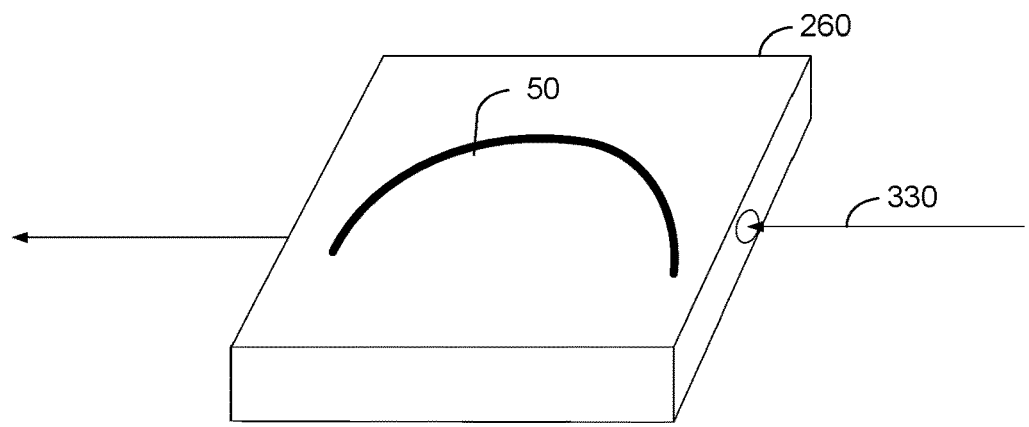
Figure 3C:
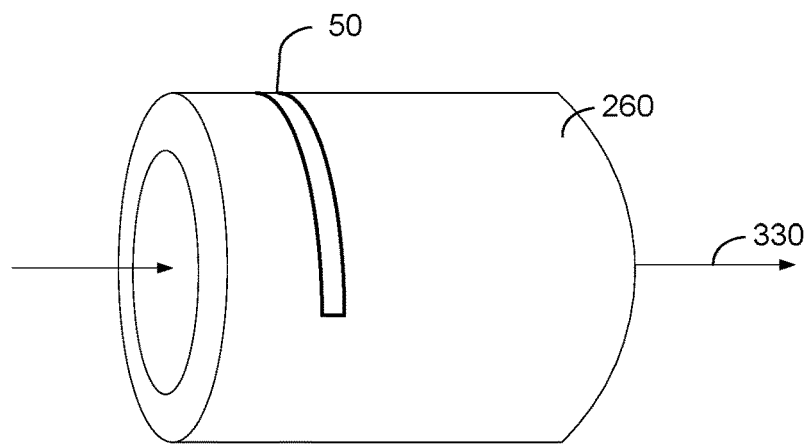

FIGS. 3A, 3B, and 3C are examples of ion implant mounting geometries for archwires.

Figure 4:
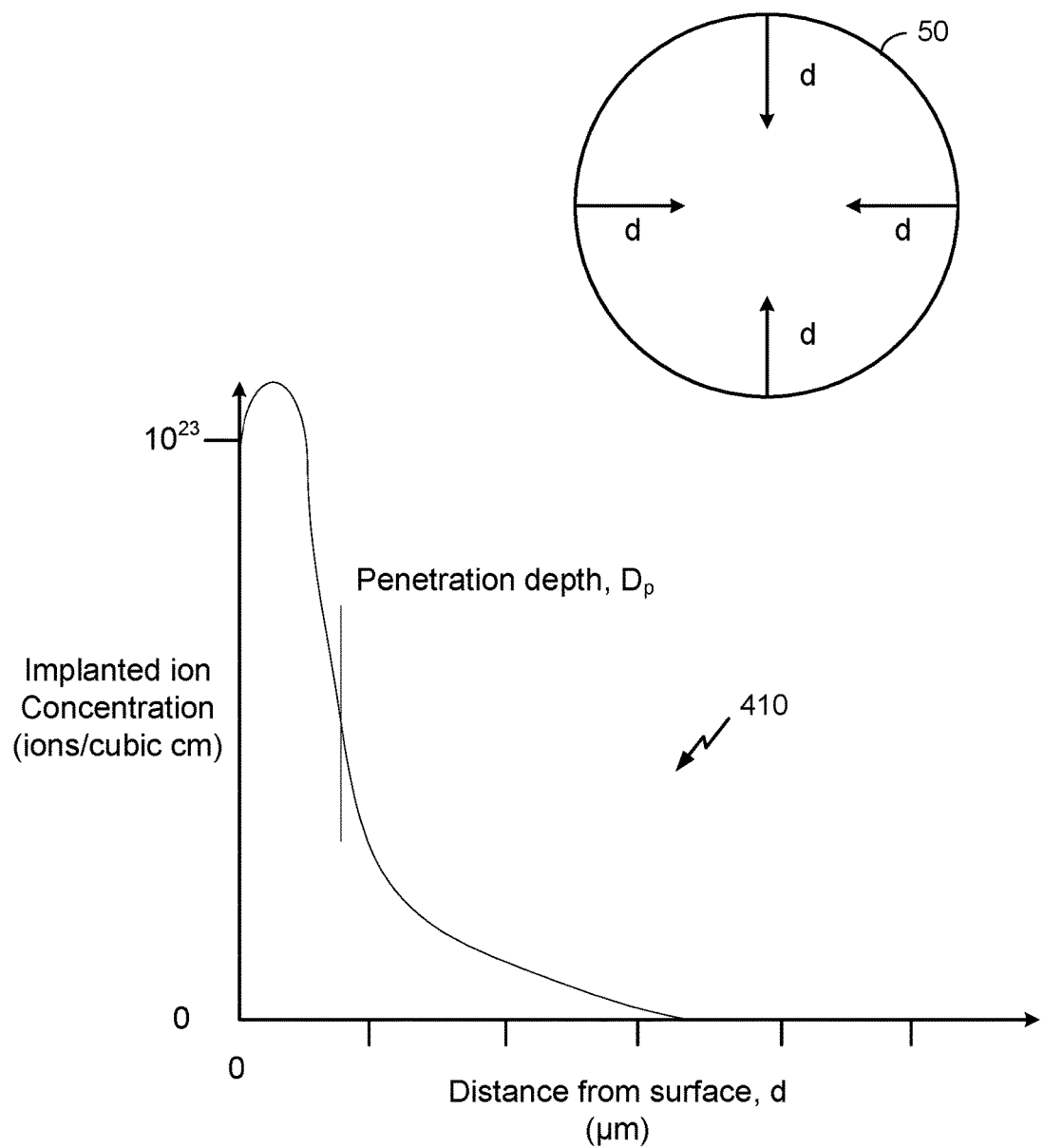

FIG. 4 is an example of a depth profile indicative of an ion implant process.

Figure 5A:
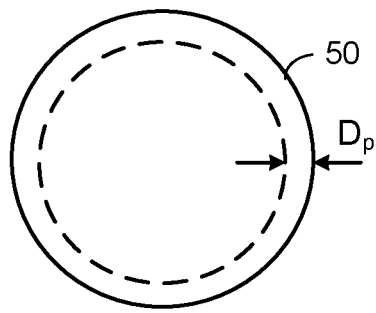
Figure 5B:
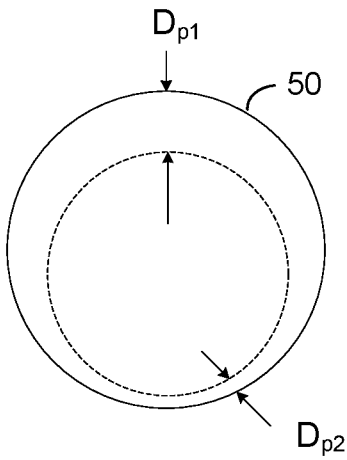
Figure 5C:
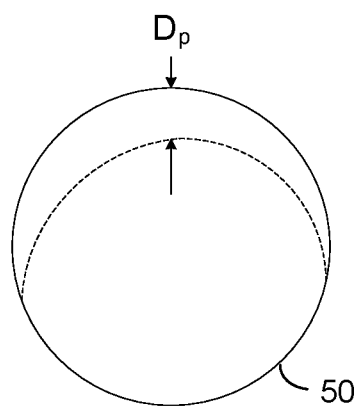

FIGS. 5A, 5B, and 5C are examples of penetration depths for ion implants corresponding to various target mounting geometries.

FIG. 6 is a table of examples of ion implant parameters for an ion implanted process used to modify an appearance of a wire target.

Figure 7:
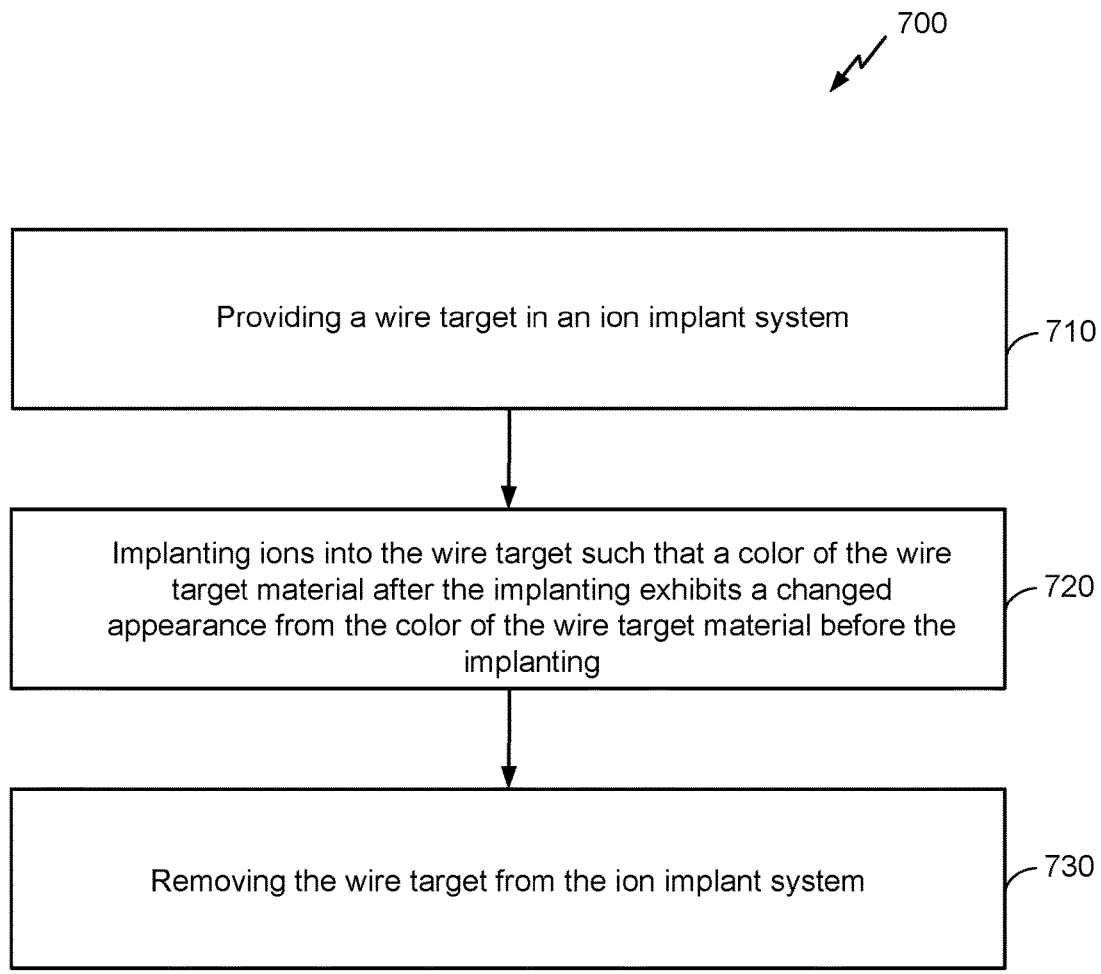

FIG. 7 is block diagram of an example of a method of ion implanting a wire target.

Figure 8:
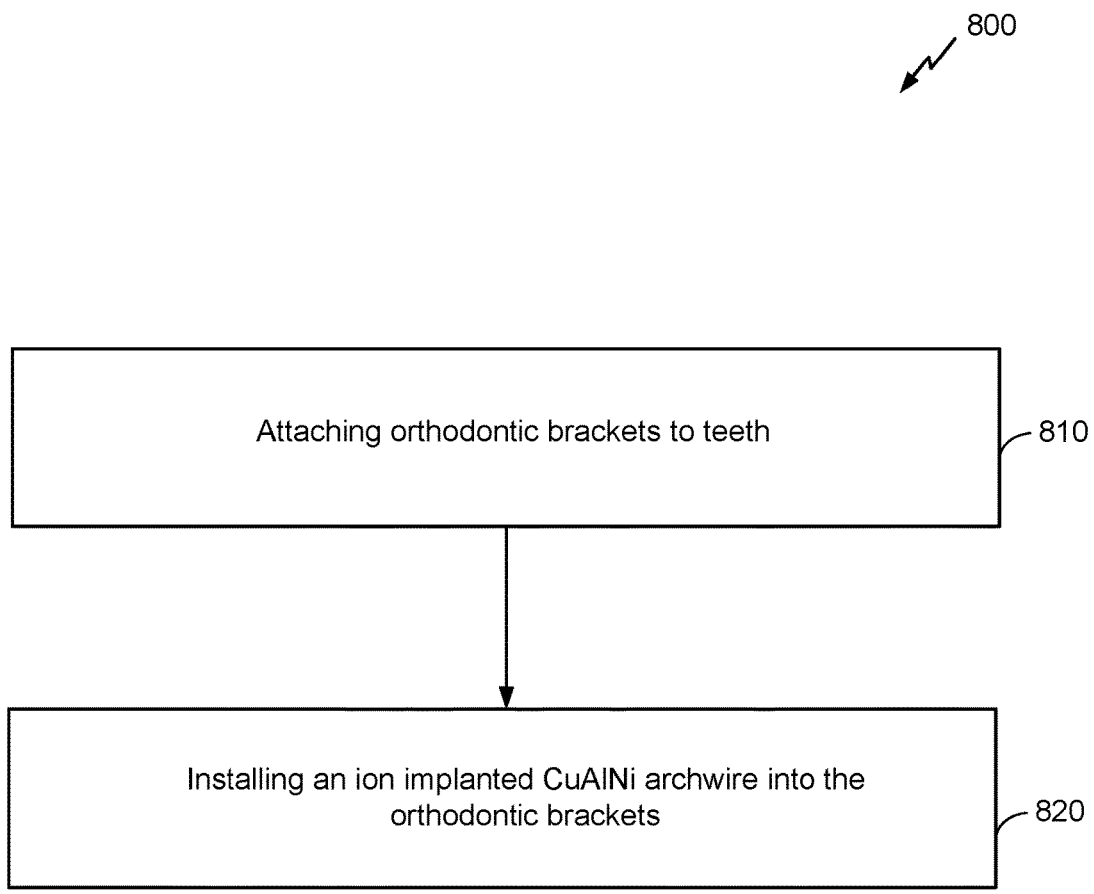

FIG. 8 is a block diagram of an example of a method of using an ion implanted wire target.

DETAILED DESCRIPTION

Techniques are provided for modifying an appearance of an orthodontic archwire using ion implantation. The techniques discussed below are exemplary, however, and not limiting of the invention as other implementations in accordance with the disclosure are possible.

Figure 1:
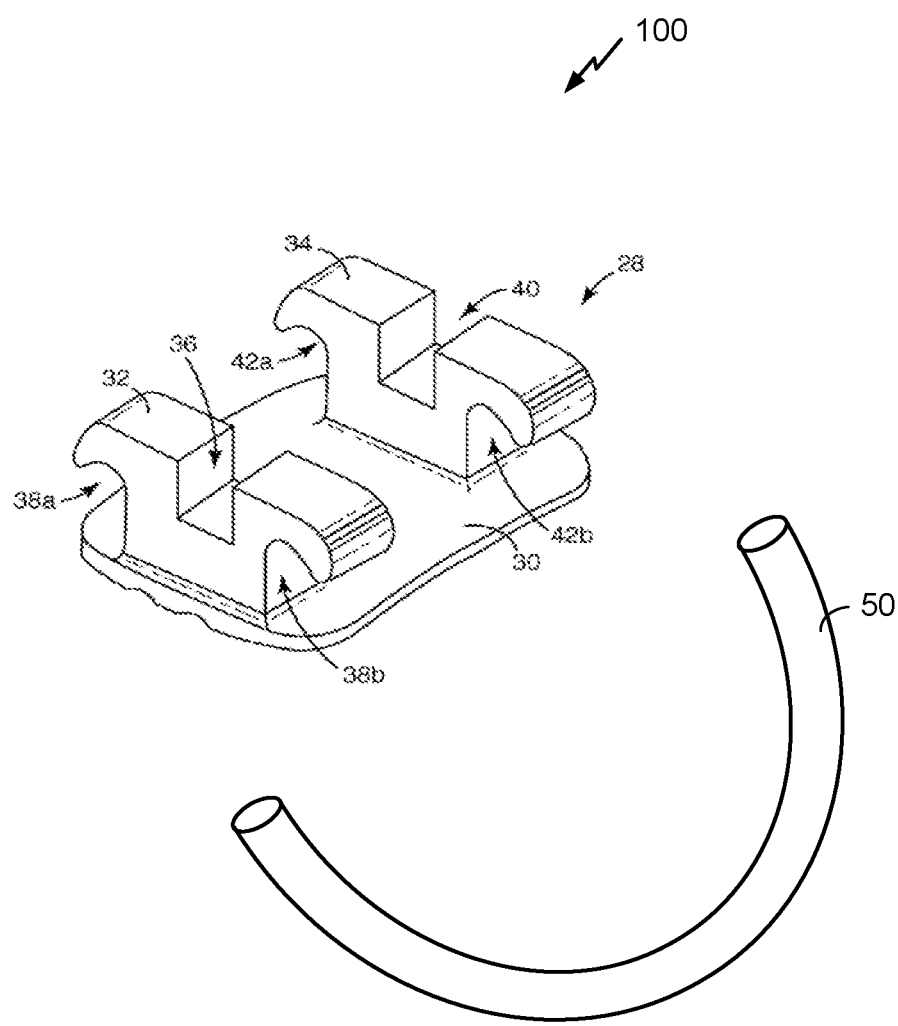
FIG. 1 is a schematic diagram of an example of an orthodontic appliance system.

Referring to FIG. 1, a schematic diagram of an example of an orthodontic appliance system is shown. The system 100 is an example and not limiting and may be altered, e.g., by having components added, removed, or rearranged. A quantity of each component in FIG. 1 is an example only and other quantities of each, or any, component could be used. The orthodontic appliance system 100 includes an archwire 50 and a bracket 28. The bracket 28 may include base 30 and tie-wings 32 and 34. Base 30 is the portion of bracket 28 that becomes bonded to a tooth surface. Tie-wings 32 and 34 are a pair of wing-like structures integrally connected to base 30 for retaining the archwire 50. The dimensions of tie-wing 32 may define slot 36 and ligature recesses 38a and 38b. Similarly, the dimensions of tie-wing 34 may define slot 40 and ligature recesses 42a and 42b. Slots 36 and 40 may be the portions of bracket 28 that may engage the archwire 50. Ligature recesses 38a, 38b, 42a, and 42b may be configured to receive a standard elastomeric or wire ligature for retaining the archwire 50 within slots 36 and 40. In use, an orthodontist may place a portion of the archwire 50 within slots 36 and 40. A ligature may then be placed over the archwire 50 and into recesses 38a and 38b behind tie-wing 32 and recesses 42a and 42b behind tie-wing 34. This process may secure the archwire within slots 36 and 40. An upper or lower orthodontic brace generally includes a plurality of brackets 28. Each bracket is bonded to a single tooth of the upper or lower dental arch and the archwire 50 may extend around the dental arch to engage with each bracket. The forces applied by the archwire 50 on the teeth through the brackets may move a patient's teeth for the purpose of aligning or straightening them. The mechanical properties of the archwire 50 enable the application of these forces. The archwire 50 may be characterized by a cross-sectional geometry, a diameter, and a constituent material. Examples of cross-sectional geometries of the archwire 50 include, but are not limited to, elliptical, circular, square, rectangular, and beveled. Elliptical and circular archwires commonly have an axis dimension or diameter of approximately 0.010-0.022 inches. Rectangular or square archwires commonly have side dimensions of 0.010 to 0.028 inches.

Materials of interest as a constituent material for the archwire 50 are shape memory alloys (SMAs), including, for example, a copper-aluminum-nickel (CuAlNi) alloy. The shape memory properties of CuAlNi may offer advantages over other archwire materials that exhibit poor or no shape memory properties (e.g., stainless steel). In typical orthodontic treatment of teeth, the orthodontic archwire, is deformed and bent into a particular shape by an orthodontist so as to exert a particular force or forces on the orthodontic brackets attached to the teeth. However, non-SMA archwires may have relatively low shape recovery, and the force applied by the wire may vary substantially as the teeth move. In the absence of shape recovery or shape memory by the archwire, the changes in force may require archwire adjustment or replacement by the orthodontist at different and multiple points during the straightening process.

A SMA such as, for example, the CuAlNi alloy, exhibits shape memory properties which are desirable for the archwire 50. SMAs often exhibit pseudoelastic and/or superelastic characteristics. The stress-strain behavior of pseudoelastic and/or superelastic materials may allow recovery of up to 6% strain, well beyond conventional stainless steels. In general, the SMAs are materials which have the ability to return to a predetermined shape when heated. When the SMAs are below their transformation temperature, they exhibit relatively low yield strengths and may be deformed into and/or retain a new shape relatively easily. However, when the SMAs are heated above their transformation temperature, they undergo a change in crystal structure, or phase transformation, which may cause them to return to their original shape. During the phase transformation, SMAs may either generate a relatively large force against any encountered resistance or undergo a significant dimension change when unrestricted. More specifically, SMAs may undergo a reversible crystalline phase transformation from a martensitic phase to an austenitic phase when heated through a particular temperature range. The reversible phase transformation may permit SMAs to be deformed at one temperature and then heated to an elevated temperature where the SMA may recover all or nearly all of its pre-deformed or original shape. Generally, martensite is soft and ductile while austenite is rigid and elastic. Because these two phases provide different mechanical properties, the temperature of the alloy during use dictates the mechanical properties of the alloy according to the proportions of martensite and austenite. Therefore, the phases present when the orthodontic archwire is at the temperature of the human body may determine the mechanical properties of the archwire. The composition of the alloy, the thermal treatment of the alloy, and/or the stresses induced into the alloy during manufacturing may establish the transformation properties (e.g., transformation temperature and stress-strain curve characteristics) of the SMA and the orthodontic archwire fabricated from the SMA.

In the orthodontic archwire application, the force generated during the phase transformation of the SMA may provide sufficient force to realign teeth. For example, the archwire may be formed into a U-shape at a temperature above a phase transition temperature of the archwire. The U-shape may correspond to a desired aligned shape of the patient's teeth. The archwire may be cooled to room temperature and deformed at room temperature to tie into orthodontic brackets on the patient's teeth. The phase transition temperature of the archwire may be above room temperature but less than or approximately equal to the temperature in the patient's mouth. The archwire temperature may increase while the archwire is in the patient's mouth. As the archwire temperature exceeds the transition temperature, the warmer wire may exert forces on the teeth as it resumes its original U-shape.

Despite the advantages of the SMA properties of CuAlNi alloys, a drawback of the CuAlNi alloy is that the reddish brown copper color associated with this alloy is aesthetically displeasing to many orthodontic patients as the archwire 50. The copper color may not match or blend with a color often associated with teeth and/or bracket materials including aluminum alloys, stainless steel alloys, etc. Ion implantation can alter the color of the CuAlNi wire without adversely affecting the physical and mechanical properties of the wire. The ion implanted CuAlNi alloy wire may exhibit mechanical properties characteristic of an unimplanted CuAlNi alloy wire. Examples of these properties may include yield strain, hardness, Young's modulus, bend resistance, roughness, expansion, internal friction, lattice spacing, electrical resistance, thermal conductivity, heat capacity, etc. The color of the CuAlNi wire before the ion implantation may be different than the color of the CuAlNi wire after the ion implantation. For example, before the implantation the color of the CuAlNi wire may be the copper color. After the implantation, the CuAlNi wire may exhibit an off-white, white, and/or silver color rather than the copper color. These colors may blend with natural tooth colors and orthodontic bracket colors to provide a color aesthetically pleasing to patients, orthodontists, and/or other observers of the orthodontic archwire. The altered color of the archwire 50 may be determined by visual inspection (i.e., by a human eye). Additionally, reflectance spectrometry measurements for the ion implanted archwire may be different than the spectral reflectance curve indicative of a copper colored material. For example, the spectral reflectance curve may correspond to a spectral reflectance curve indicative of a white, off-white, and/or silver colored material.

In order to take advantage of the SMA properties of CuAlNi and provide the color change of the archwire 50, C ions and/or other ionized atomic species may be implanted into CuAlNi archwires. The ion implant process and/or chemical and/or microstructural properties of the CuAlNi alloy caused by and/or induced by the ion implant process may change the appearance (e.g., the color) of the CuAlNi archwire. During the ion implant process, ions bombard and penetrate a substrate or target surface. The ions interact with the atoms of the target or substrate in a region proximate to and including the surface of the target. This penetration region is described in further detail below with regard to FIG. 4. The interactions of the energetic ions with the target material may modify one or more properties of the target material. The particular properties and the modifications of these properties may depend on various parameters of the ion implant process (e.g., ion species, ion beam energy, ion beam dose, ion beam dose rate, implant time, implant temperature, arrival rate, etc.).

Ion implant may enable a low-temperature ion implant process. In various embodiments, "low temperature" refers to processes that maintain a target temperature of less than or equal to approximately 300° C., less than or equal to approximately 200° C., or less than or equal to approximately 100° C. The low temperature of the ion implant process may contribute to producing the desired color change while maintaining the desirable mechanical properties of the CuAlNi wire. The desirable mechanical properties of the CuAlNi wire may be mechanical properties subsequent to the ion implant that are substantially similar to mechanical properties exhibited by the wire prior to the ion implant. In particular, the desirable mechanical properties of the CuAlNi wire may be the SMA properties compatible with orthodontic applications. The transformation temperature and the mechanical properties (e.g., yield strain, Young's modulus, hardness, bend resistance, roughness, thermal expansion, etc.) may depend on the microstructure (e.g., grain size, crystal structure, composition, point defect distribution, etc.). Therefore, the temperature during ion implant may be low enough so as not to alter the microstructure of the archwire. Additionally, the archwires may be implanted in a shape introduced below the transformation temperature. In this case, the temperature during the ion implant may be kept below the transformation temperature in order to prevent shape memory behavior (i.e., temperature induced shape changes) prior to installation of the archwire in the patient's mouth. As additional benefits, ion implant may provide a high-throughput and reproducible process for modifying the CuAlNi archwire color.

Figure 2:
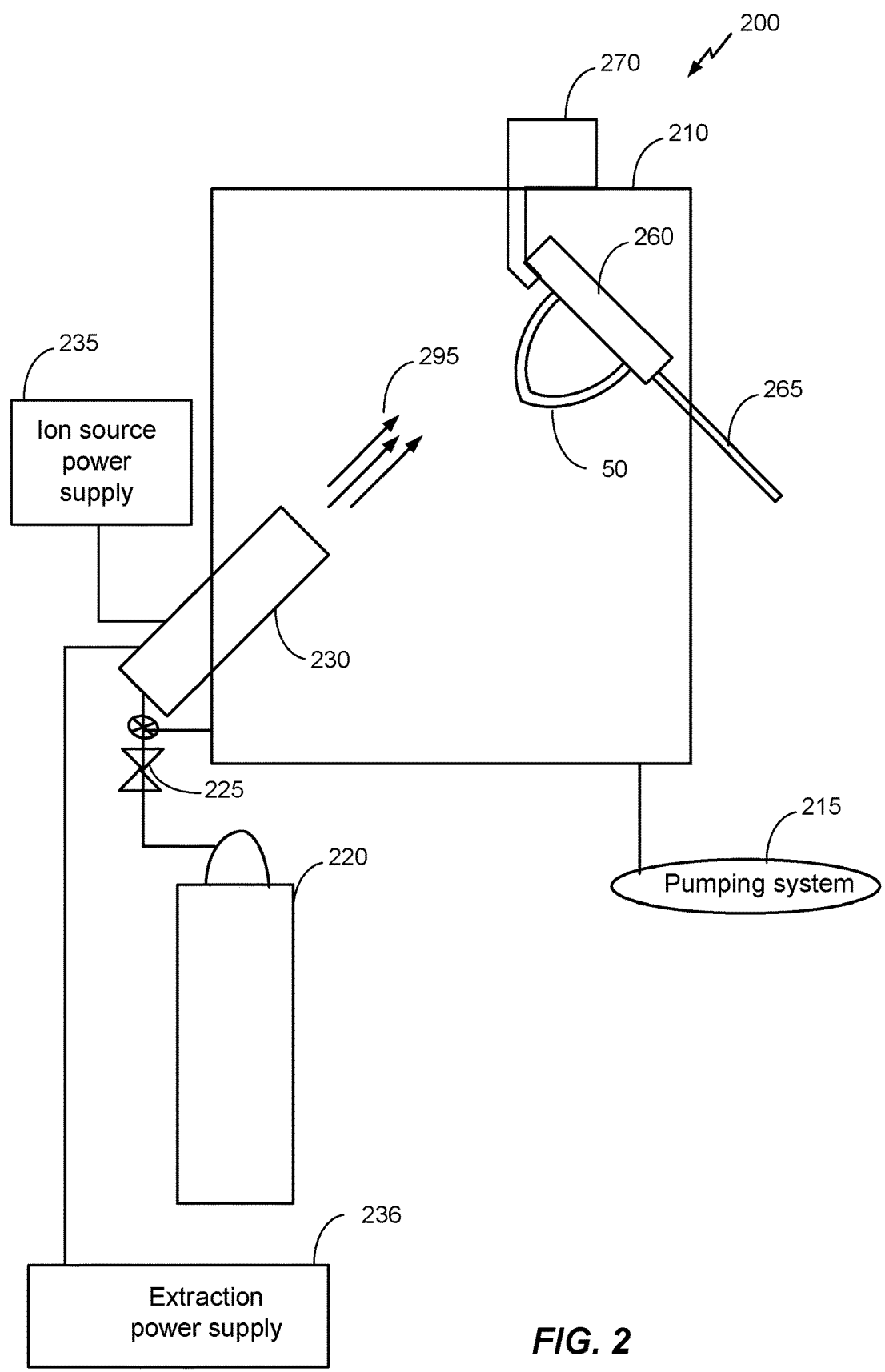
FIG. 2 is a schematic diagram of an example of an ion implant system.

Referring to FIG. 2, a schematic diagram of an example of an ion implant system is shown. The system 200 is an example and not limiting and may be altered, e.g., by having components added, removed, or rearranged. A quantity of each component in FIG. 2 is an example only and other quantities of each, or any, component could be used. Such ion implant systems are known in the art. The system 200 is configured to provide ion bombardment of a target or substrate by ions in an accelerated ion beam in order to implant the ions into the target or substrate. The system 200 may include a vacuum chamber 210, an ion source 230, a pumping system 215 and a gas supply source 220. The ion source 230 may be any suitable ion source for ion implant and may be coupled to an ion source power supply 235. An extraction power supply 236 may be configured to accelerate the ions to form an accelerated ion beam 295. A series of electrostatic and/or magnetic lens elements (not shown) may shape the ion beam 295 and may cause the ion beam 295 to scan over one or more targets disposed on the target holder 260. The ion beam energy may be 10-200 kilo-electron volts (keV). The extraction power supply 236 may determine the ion beam energy. The ions in the accelerated ion beam may originate from a gaseous and/or non-gaseous supply source coupled to and/or included in the ion source 230. For example, the gas supply source 220 may provide gaseous species for use by the ion source 230 in generating accelerated ionic species. The gas supply source 220 may be coupled to a mass flow controller 225. A flow rate as controlled by the mass flow controller may be less than or equal to 100 cubic centimeter per minute (ccm). In an implementation, the gas supply source 220 may provide a source of one or more backfill gases in the vacuum chamber 210. As another example, a non-gaseous species in a vaporizer (not shown) coupled to and/or included in the ion source may provide atomic and/or molecular species (e.g., via thermal, chemical, and/or other vaporization methods) for use by the ion source 230 in generating the ionic species in the accelerated ion beam. Operating conditions of the extraction power supply 236, the ion source 230, the ion source power supply 235 and/or the mass flow controller 225 may determine the arrival rate of the ion beam 295. The ion beam 295 may include one or more ionized atomic and/or molecular species. The ionized atomic and/or molecular species in the ion beam 295 may provide the species implanted into a target disposed at the target holder 260. The implanted species may include, for example, but not limited to, C, CO, Si, O, F, N, B, H and/or combinations thereof.

The archwire 50 may be the target disposed at the target holder 260. The target may be introduced into the vacuum chamber 210 with the aid of the target holder 260. The target holder 260 may be mounted on a shaft 265 that may provide rotational and/or translational motion. Although ion implant is a line-of-sight process, the target holder 260 may be configured to enable ion implantation of targets with complex geometries. Further, the target holder 260 may be configured to facilitate or provide heat dissipation and/or target temperature control. A temperature monitor 270 may be configured to monitor the temperature of the archwire 50 and/or the target holder 260 during the ion implant process. The temperature of the archwire 50 during the ion implant process may be a temperature at which the mechanical properties of the wire are substantially unchanged by the ion implant process. In an example, the temperature of the archwire 50 during the ion implant may be below 300° C. In a further example, the temperature of the archwire 50 during the ion implant may be below 200° C. In order to maintain a particular target temperature, the wire may be cooled during the ion implant.

Referring to FIGS. 3A, 3B, and 3C, examples of ion implant mounting geometries for archwires are shown. In these examples, one archwire is shown for simplicity, but one or more archwires may be mounted to the target holder 260 and/or one or more archwires 50 may be implanted concurrently. In the example of FIG. 3A, the archwire 50 is removably attached at either end to the target holder 260 with an open space 390 between the target holder 260 and the archwire 50. In the examples of FIGS. 3B and 3C, the archwire 50 is mounted such that at least a portion of the archwire 50 in contact with the target holder 260 along the length of the archwire 50. In the example of FIG. 3B, as the archwire 50 is disposed on the surface of a slab shaped target holder 260. In this geometry, archwire 50 may be conductively cooled by a water flow 330 through the slab shaped target holder 260. In the example of FIG. 3C, the archwire 50 is wrapped around a cylindrical target holder 260. In this geometry, the archwire 50 may be conductively cooled by a water flow 330 through the cylindrical target holder 260. In addition to and/or as an alternative to controlling the target temperature with target holder cooling, other ion implant parameters, as discussed in more detail below, may be adjusted to maintain the particular target temperature.

A depth profile of one or more atomic and/or molecular species ion implanted into the archwire 50 may exhibit features indicative of the ion implant process. Referring to FIG. 4, an example of a depth profile indicative of an ion implant process is shown. The depth profile 410 is an ion concentration as a function of distance, d, from the target surface inward towards the bulk of the target. The penetration depth, $D_p$, is the distance from the target surface corresponding to a particular implanted ion concentration. The depth profile and/or the penetration depth may define the ion implanted region of the archwire 50. Typically, the ion concentration is measured in units of ions per cubic centimeter and the distance from the surface, d, is measured in micrometers (e.g., abbreviated as μm wherein 1 μm=1× $10^{-6}$ meters). For the circular archwire 50, the distance from the surface d may be a radial distance. The penetration depth may vary along the surface of the archwire 50. The variation may depend on the particular geometry of the target in the target holder and on the ion implant process parameters.

Referring to FIGS. 5A, 5B, and 5C, examples of penetration depths for ion implants corresponding to various target mounting geometries are shown. The penetration region of the ion implant may exhibit an approximately uniform penetration depth, $D_p$, around the circumference of the archwire 50, as shown schematically in FIG. 5A, or may vary around the circumference, as shown schematically in FIG. 5B. In FIG. 5B, the penetration depth, $D_{p1}$, at some points around the circumference may be greater than the penetration depth, $D_{p2}$, at other points around the circumference. For example, the arched mounting geometry in FIG. 3A may produce a circumferential penetration region similar to FIG. 5A and/or FIG. 5B. As another example, the mounting geometry in FIGS. 3B and/or 3C may produce a penetration region similar to that shown in FIG. 5C. If the archwire 50 is mounted with one side of the wire being in contact with the target holder 260, as shown for example in FIGS. 3B and 3C, then the penetration region of the ion implant may be substantially limited to a portion of the archwire 50 facing away from the target holder 260. The penetration depth and circumferential profile of the implanted ions in the archwire may determine the portion of the archwire that exhibits the appearance modification following the ion implant. However, in practice only this portion of the archwire may be visible when mounted in the orthodontic bracket.

The implant parameters may be adjusted to provide the desired appearance modification without substantially changing the mechanical properties of the wire target. Referring to FIG. 6, a table of examples ion implant parameters for an ion implant process used to modify an appearance of a wire target is shown. The ion beam parameters may include an ion beam dose, D, an ion beam dose rate, R, an ion implant duration, T, and an ion beam energy, E. In various implementations, the ion implant parameters may be within a parameter space as delineated in FIG. 6. In the example of FIG. 6, the ion beam dose is indicated as multiples of D=5E16 ions/cm², the ion beam dose rate is indicated as multiples of R=0.1 μA/cm²/sec, the ion implant duration is indicated as multiples of T=1 hour, and the ion beam energy is indicated as multiples of E=80 keV. In an embodiment the time, T, may be in a range of 0.4-12 hours as indicated in FIG. 6. In other embodiments, the time T may be less than or equal to 35 hours and/or may be determined by or based on the ion dose, dose rate, an ion beam current density, and/or an ion beam current. For example, a lower current density may be associated with a longer implant time, T. In various implementations of the ion implant process used to modify the color of the wire target, the total dose used for the ion implant process may range from 1E15-1E18 ions/cm², from 1E15-1E16 ions/cm², from 1E16-1E17 ions/cm², or from 1E17-1E18 ions/cm². In various implementations of the ion implant process used to modify the color of the wire target, the arrival rate of the ion beam may be in a range between about 0.025 to about 10 microamperes per square centimeter per second (μA/cm²/sec) and/or the ion beam energy may be in a range from 10-200 keV. In an implementation, the ion implant parameters may correspond to an ion beam dose of approximately 5E16 C ions/cm², an ion beam dose rate of approximately 0.1 μA/cm²/sec, a one hour ion implant duration, and an ion beam energy of approximately 80 keV. The ion implant parameters may be adjusted to reduce or eliminate changes in the microstructure and/or the composition of the CuAlNi wire as induced by the ion implant process. The penetration depth for the implanted ions for the operating conditions in FIG. 6 may be approximately ≤1 µm. The implanted species may be one or more atomic and/or molecular species, including, for example, but not limited to C, CO, Si, O, F, N, B, H and/or combinations thereof.

Referring to FIG. 7, with further reference to FIGS. 1-6, a method of ion implanting a wire target is shown. The method 700 is, however, an example only and not limiting. The method 700 can be altered, e.g., by having stages added, removed, rearranged, combined, performed concurrently and/or having stages split into multiple stages.

At stage 710, a method 700 includes providing a wire target in an ion implant system. For example, the wire target may be the CuAlNi wire or other shape memory alloy. The wire target may be an orthodontic archwire. The wire target may be shaped for orthodontic archwire applications prior to ion implant and, therefore, may be implanted as an individual archwire. In an implementation, a length of wire exceeding an orthodontic archwire length may be implanted and subsequently cut and shaped for use as an orthodontic archwire. The stage 720 may include evacuating the ion implant vacuum chamber 210 to a pressure suitable for ion implant. For example, the pressure of the ion implant vacuum chamber 210 during the ion implant process may be $10^{-4}$ to $10^{-5}$ Torr.

At stage 720, the method 700 includes implanting ions into the wire target such that a color of the wire target material after the implanting exhibits a changed appearance from the color of the wire target material before the implanting. The implanted ions may be one or more ionized atomic and/or molecular species, including, for example, but not limited to C, CO, Si, O, F, N, B, H and/or combinations thereof.

The implant parameters of ion beam dose, ion beam dose rate, ion implant duration, and/or ion beam energy may correspond to parameters that produce the color change of the wire target. For example, the implant parameters may be chosen from the parameter space described above with regard to FIG. 6. In an embodiment, the stage 720 may include maintaining the temperature of the wire target at or below a particular temperature. The particular temperature may correspond to a transformation temperature of the wire target. The particular temperature may be below 300° C., below 200° C., or below 100° C. The particular temperature may limit microstructural changes in the wire target such that mechanical properties of the wire are substantially unchanged by the ion implant process.

At stage 730, the method 700 includes removing the wire target from the ion implant system. The stage 730 may include a vacuum venting step. Subsequently, the target may exit the high vacuum operating environment and be retrieved from a material output section. The wire target may be provided to orthodontists and/or distributors/manufacturers of orthodontic and/or other wire supplies.

Referring to FIG. 8, with further reference to FIGS. 1-7, an example of a method of using an ion implanted wire target is shown. The method 800 is, however, an example only and not limiting. The method 800 can be altered, e.g., by having stages added and/or having a stage split into multiple stages.

At stage 810, the method 800 includes attaching orthodontic brackets to teeth. The orthodontic brackets may be any brackets suitable for orthodontic realignment of the teeth. For example, the brackets may be similar in structure and/or function to the bracket 28 shown in FIG. 1. An orthodontist may affix two or more orthodontic brackets 28 to a patient's teeth with an appropriate adhesive.

At stage 820, a method 800 includes, installing an ion implanted archwire into orthodontic brackets. The archwire may be a CuAlNi alloy wire or other shape memory alloy. The ion implanted CuAlNi archwire may exhibit a color that is different from a copper color typical of CuAlNi alloys and/or may be a C ion implanted CuAlNi archwire. The color of the CuAlNi archwire may be a white, off-white and/or silver color. The color of the CuAlNi archwire may be similar to the color of orthodontic brackets and/or teeth. The orthodontist may engage an archwire 50 into orthodontic brackets (e.g., the archwire may be inserted into slots 36 and 40 of each bracket 28 as shown in FIG. 1). The archwire 50 may exert flexural and/or torsional stresses on the orthodontic brackets 28 to create restorative forces, including rotation, tipping, extrusion, intrusion, translation, and/or torque forces, tending to bring the teeth toward a desired position.

Other Considerations

The methods, systems, and devices discussed above are examples and other embodiments are within the scope of the invention. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure.

Specific details are given in the description to provide a thorough understanding of example configurations (including implementations). However, configurations may be practiced without these specific details. For example, well-known processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure.

Having described several example configurations, various modifications, alternative constructions, and equivalents may be used without departing from the disclosure. For example, the above elements may be components of a larger system, wherein other rules may take precedence over or otherwise modify the application of the invention. Also, a number of operations may be undertaken before, during, or after the above elements are considered. Also, technology evolves and, thus, many of the elements are examples and do not bound the scope of the disclosure or claims. Accordingly, the above description does not bound the scope of the claims. Further, more than one invention may be disclosed.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition. As used herein, including in the claims, unless otherwise stated, a statement that a function or operation is "based on" an item or condition means that the function or operation is based on the stated item or condition and may be based on one or more items and/or conditions in addition to the stated item or condition.

What is claimed is:

1. A method of ion implanting a wire target comprising:
providing the wire target within a line-of-sight of an ion beam in an ion implant system;
implanting ions into the wire target with the ion beam at an ion beam energy of 10-200 keV such that a color of the wire target material after the implanting exhibits a changed appearance from the color of the wire target material before the implanting; and
removing the wire target from the ion implant system.

2. The method of claim 1 wherein the wire target is a copper-aluminum-nickel (CuAlNi) alloy.

3. The method of claim 1 wherein the implanting ions comprises implanting ions at an ion beam dose of 1E15-1E18 ions/$cm^2$, an ion beam dose rate of 0.025-10 $\mu A/cm^2$/sec, and an ion implant duration of 0.4-12 hours.

4. The method of claim 1 wherein the implanting ions comprises implanting one or more of C, CO, Si, O, F, N, B, H, or combinations thereof.

5. The method of claim 4 further comprising:
implanting carbon ions at an ion beam dose of approximately 5E16 ions/$cm^2$, an ion beam dose rate of approximately 0.1 $\mu A/cm^2$/sec, an ion implant duration of approximately one hour, and an ion beam energy of approximately 80 keV.

6. The method of claim 1 further comprising maintaining a temperature of the wire target at or below a particular temperature.

7. The method of claim 6 wherein the wire target is a shape memory alloy and the particular temperature corresponds to at least one of a transformation temperature of the wire target or a temperature below 300 degrees Celsius.

8. The method of claim 1 wherein mechanical properties of the wire target are substantially unchanged by the implanting ions into the wire target.

* * * * *